(12) United States Patent
Kappagoda

(10) Patent No.: US 7,651,707 B2
(45) Date of Patent: Jan. 26, 2010

(54) METHOD FOR LOWERING BLOOD PRESSURE IN PRE-HYPERTENSIVE INDIVIDUALS AND/OR INDIVIDUALS WITH METABOLIC SYNDROME

(75) Inventor: Chulani Tissa Kappagoda, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/528,937

(22) Filed: Sep. 27, 2006

(65) Prior Publication Data

US 2007/0071841 A1 Mar. 29, 2007

Related U.S. Application Data

(60) Provisional application No. 60/721,720, filed on Sep. 28, 2005.

(51) Int. Cl.
 *A61K 36/87* (2006.01)
 *A61K 36/00* (2006.01)

(52) U.S. Cl. .......................... 424/776; 424/725

(58) Field of Classification Search .................. None
 See application file for complete search history.

(56) References Cited

U.S. PATENT DOCUMENTS

| | | | |
|---|---|---|---|
| 5,879,730 A | | 3/1999 | Bouwens |
| 6,544,581 B1 * | | 4/2003 | Shrikhande et al. ......... 426/655 |
| 6,706,756 B1 | | 3/2004 | Fitzpatrick |
| 2002/0192314 A1 | | 12/2002 | Cho et al. |
| 2003/0096050 A1 * | | 5/2003 | Inaoka et al. .............. 426/597 |
| 2003/0133992 A1 * | | 7/2003 | Bagchi et al. .............. 424/643 |

| | | | |
|---|---|---|---|
| 2004/0247714 A1 | | 12/2004 | Roe et al. |

FOREIGN PATENT DOCUMENTS

| | | | |
|---|---|---|---|
| JP | 2003-212783 | * | 7/2003 |
| WO | 2005122793 A1 | | 12/2005 |
| WO | 2006016383 A1 | | 2/2006 |

OTHER PUBLICATIONS

Preuss et al. (Ann. NY Acad. Sci (2002), vol. 957, pp. 250-259).*
www.polyphenolics.com/store/index.php—accessed Jul. 23, 2007.*
Careri et al. (J. Agric. Food Chem (2003), vol. 51, pp. 5226-5231).*
Registry Entry for Resveratrol -2008.*
Caridi, A. et al "Influence of Yeast on Polyphenol Composition of Wine" Food Technol. Biotechnol. (2004) vol. 42:1, pp. 37-40.
Nakamura, Y. et al "Analysis of Proanthocyanidins in Grape Seed Extracts, Health Foods and Grape Seed Oils", Journal of Health Science, (2003) vol. 49:1 pp. 45-54.

(Continued)

*Primary Examiner*—Patricia Leith
(74) *Attorney, Agent, or Firm*—Kenyon & Kenyon LLP

(57) ABSTRACT

The present invention relates to a method of treating Metabolic Syndrome and/or the conditions that comprise Metabolic Syndrome by administering to a mammal, including a human, a dietary supplement comprising grape extract. This invention also relates to a method of treating pre-hypertension by administering to a mammal, including a human, a dietary supplement comprising grape extract.

35 Claims, 2 Drawing Sheets

Changes in systolic blood pressure

OTHER PUBLICATIONS

Prior, R. L. et al "Occurrence and biological significance of proanthocyanidins in the American diet," Phytochemistry (2005) vol. 66:18, pp. 2264-2280.

Singleton, V. L., et al, "Analysis of total phenols and other oxidation substrates and antioxidants by means of Folin-Ciocalteu Reagent," Methods in Enzymology (1999) vol. 299, pp. 152-178.

Ward, N. C. et al "The combination of vitamin C and grape-seed polyphenols increases blood pressure: a randomized, double-blind, placebo-controlled trial," Journal of Hypertension (2005) vol. 23:2 pp. 427-434.

Waterhouse, A. L., et al "A comparison of methods for quantifying oligomeric proanthocyanidins from grape seed extracts", American Journal of Enology and Viticulture (2000) vol. 51:4, pp. 383-389.

Waterhouse, A. L., et al "Determination of total phenolics," Current Protocols in Food Analytical Chemistry, John Wiley & Sons, Inc. (2002).

International Search Report from International Patent Application No. PCT/US2006/038344.

* cited by examiner

Figure 1: Changes in systolic blood pressure
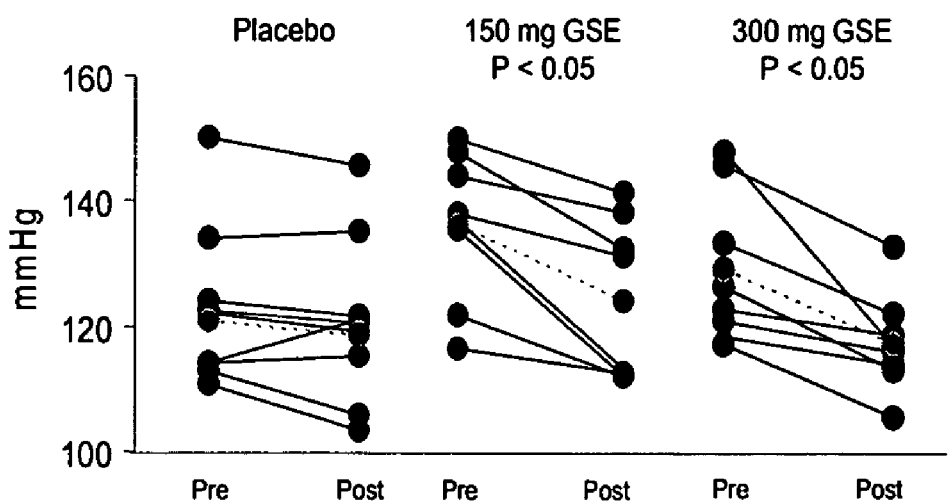
Figure 2: Changes in diastolic blood pressure
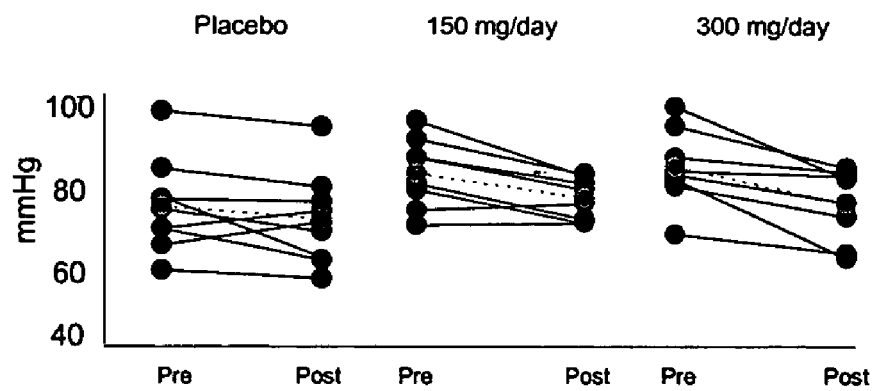

Figure 3: Changes in oxidized LDL
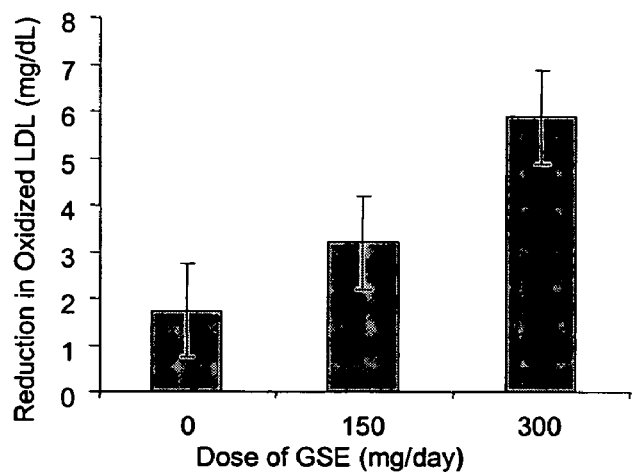
Figure 4: Relationship between the change in oxidized LDL and the baseline concentration of oxidized LDL (300 mg of MegaNatural®-BP)
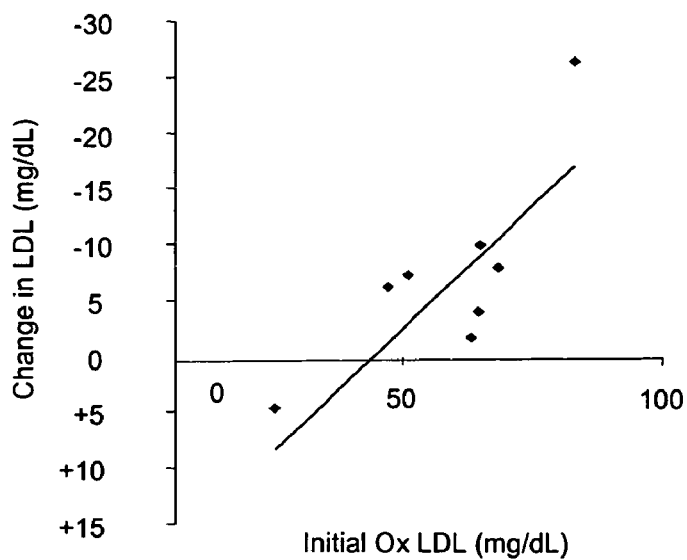

METHOD FOR LOWERING BLOOD PRESSURE IN PRE-HYPERTENSIVE INDIVIDUALS AND/OR INDIVIDUALS WITH METABOLIC SYNDROME

This application claims priority to U.S. Provisional application Ser. No. 60/721,720, filed on Sep. 28, 2005, which is incorporated by reference in its entirety.

FIELD OF THE INVENTION

This invention relates to a method of preventing and/or treating Metabolic Syndrome and/or the conditions that comprise Metabolic Syndrome. This invention also relates to a method of treating and/or preventing pre-hypertension. These methods involve administering to a mammal, including a human, a dietary supplement comprising grape extract effective for treating pre-hypertensive individuals, or individuals with Metabolic Syndrome, and/or the conditions that comprise Metabolic Syndrome.

BACKGROUND

Blood pressure is the force exerted by the bloodstream on the artery walls. Normal blood pressure is considered to be 120 systolic and 80 diastolic. Hypertension refers to a disorder that is characterized by an elevation of the systolic blood pressure to 140 and above and/or an elevation of the diastolic blood pressure to 90 and above. With hypertension, there is either an increase in the total peripheral vascular resistance such as is due to vasoconstriction, or an increase in cardiac output, or both. These conditions produce an elevation in blood pressure because blood pressure is equal to flow times resistance. There are many factors that can contribute to high blood pressure including stress, diet and lifestyle, as well as kidney complaints, hormonal disturbances and circulatory disorders. An untreated hypertensive patient is at great risk of developing left ventricular failure, myocardial infarction, cerebral hemorrhage or renal failure. Hypertension is also a risk factor for stroke and coronary atherosclerosis. Presently, hypertensive patients are treated with drug therapy that includes the use of diuretics, beta-blockers, ACE inhibitors, angiotensin antagonists, calcium channel blockers, alpha-blockers, alpha-beta-blockers, nervous system inhibitors, and vasodilators.

Pre-hypertensive individuals are classified as individuals that have systolic pressure between 120 and 139 mmHg or have diastolic pressure between 81 and 89 mmHG. This classification is based on the Seventh Report of the Joint National Committee on Prevention, Detection, Evaluation, and Treatment of High Blood Pressure (JNC 7), page 87, NIH Publication No. 04-5230. Pre-hypertensive individuals are not typically treated with drug therapy, but rather are given suggestions for a healthy lifestyle. These suggestions include maintaining a healthy weight; being physically active; following a healthy eating plan that emphasizes fruits, vegetables, and low fat dairy foods; choosing and preparing foods with less sodium; and drinking alcoholic beverages in moderation if at all. Adopting healthy lifestyle habits is usually an effective first step in both preventing and controlling abnormal blood pressure.

Many patients with hypertension are insulin resistant. Insulin stimulates glucose uptake into tissues, and its ability to do so varies greatly among individuals. With insulin resistance, tissues have a diminished ability to respond to the action of insulin. To compensate for resistance, the pancreas secretes more insulin. Insulin-resistant individuals, therefore, have high plasma insulin levels. There is evidence that abnormal blood pressure is linked to the degree of insulin resistance. The precise way in which insulin resistance develops is unclear, although genetics, diet and level of physical activity are believed to play a role.

"Metabolic Syndrome," also called "Syndrome X," the "Insulin Resistance Syndrome," or the "Deadly Quartet," is characterized by an accumulation of risk factors for cardiovascular disease, stroke and/or diabetes mellitus type II. Metabolic Syndrome may be caused by an overproduction of cortisol, a stress hormone, which causes an accumulation of fat inside the abdominal cavity and insulin resistance. Drug therapy is not currently recommended for individuals with Metabolic Syndrome. The risk factors that characterize Metabolic Syndrome include an increased amount of adipose tissue inside the abdominal cavity (abdominal obesity), insulin resistance with increased risk of developing diabetes, hyperinsulinemia, high levels of blood fats, increased blood pressure, and elevated serum lipids. The National Cholesterol Education Adult Treatment Panel (ATP III) defined Metabolic Syndrome as individuals having at least three of the following risk factors:

| Risk Factor | Defining Level |
|---|---|
| Abdominal obesity, given as waist circumference*† | |
| Men | >102 cm (>40 in) |
| Women | >88 cm (>35 in) |
| Triglycerides | ≧150 mg/dL |
| HDL cholesterol | |
| Men | <40 mg/Dl |
| Women | <50 mg/dL |
| Blood pressure | ≧130/≧85 mm Hg |
| Fasting glucose | ≧110 mg/dL‡ |

*Overweight and obesity are associated with insulin resistance and Metabolic Syndrome. The presence of abdominal obesity, however, is more highly correlated with the metabolic risk factors than is an elevated BMI. Therefore, the simple measure of waist circumference is recommended to identify the body weight component of Metabolic Syndrome.
†Some male patients can develop multiple metabolic risk factors when the waist circumference is only marginally increased, e.g., 94 to 102 cm (37 to 39 in). Such patients may have a strong genetic contribution to insulin resistance. They should benefit from changes in life habits, similarly to men with categorical increases in waist circumference.
‡The American Diabetes Association has recently established a cut-off point of ≧100 mg/dL, above which individuals have either pre-diabetes (impaired fasting glucose) or diabetes. This new cut-off point should be applicable for identifying the lower boundary to define an elevated glucose as one criterion for Metabolic Syndrome.

The World Health Organization, however, defines Metabolic Syndrome as individuals with diabetes/insulin resistance and at least two of the following risk factors: high waist-to-hip ratio; high triglycerides or low HDL cholesterol; high blood pressure; and a high urinary albumin excretion rate.

Conditions related to Metabolic Syndrome include diabetes mellitus type II, dyslipoproteinemia, myocardial infarction, stroke and other arteriosclerotic diseases, as well as the risk factors for these diseases, including insulin resistance in general, abdominal obesity caused by accumulation of intra-abdominal fat, elevated blood serum lipids and glucose, raised diastolic and/or systolic blood pressure, and hypertension.

Treatment of pre-hypertensive individuals and individuals with Metabolic Syndrome are encouraged to adopt a healthy lifestyle, which includes maintaining a healthy weight; being physically active; and following a healthy eating plan. Given that drug therapy is not recommended to these individuals, there is a need for a dietary supplement comprising grape extract that these individuals can use as adjunctive therapy, which is effective in lowering blood pressure and does not increase insulin resistance.

Grape seeds contain about 5-8% by weight flavonoids. Flavonoids constitute an important group of dietary polyphenolic compounds that are widely distributed in plants. More than 4000 chemically unique flavonoids have been identified in plant sources, such as fruits, vegetables, legumes, nuts, seeds, herbs, spices, flowers, as well as in beverages such as tea, cocoa, beer, wine, and grape juice.

The terminology of flavonoids with respect to grape seeds refers to monomeric flavan-3-ols, specifically (+)-catechin, (−)-epicatechin, and (−)-epicatechin 3-gallate. Two or more flavan-3-ol monomers chemically linked are called proanthocyanidins or oligomeric proanthocyanidins ("OPCs"), which includes procyanidins and prodelphinidins. OPCs containing two monomers are called dimers, three monomers are called trimers, four monomers are called tetramers, five monomers are called pentamers, etc. Operationally, the oligomers have chain lengths of 2 to 7 (dimers to heptamers); whereas polymers represent components with chain lengths greater than 7. After considerable discussion, it was the consensus of the Grape Seed Method Evaluation Committee (through the National Nutritional Foods Association) to define OPCs as all proanthocyanidins containing two or more monomers, including polymers or condensed tannins. Thus, oligomers in grape extracts include, for instance, dimers and trimers, and there is evidence that the polymers can have as many as sixteen units.

Below is a typical structure of a proanthocyanidin, showing epicatechin-gallate extension units and terminal units. The extension units are represented, for instance, by the epicatechin (2) and epigallocatechin (3) linking groups. Whereas, a terminal unit is represented by the epicatechin gallate (4) group.

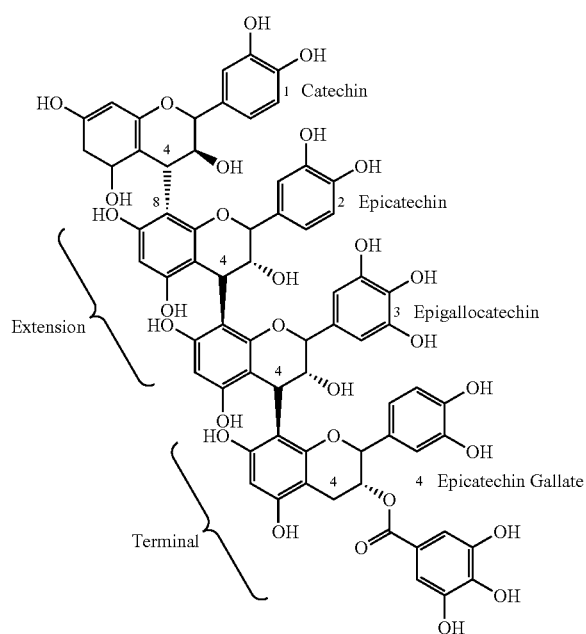

In order for polyphenolic compounds to be used commercially as a grape extract, these compounds have to be separated from grapes in a more concentrated form. The general process in which the polyphenolic compounds are extracted, purified and concentrated from whole grapes, grape pomace and grape seeds is disclosed in U.S. Pat. No. 6,544,581, which is incorporated herein by reference.

BRIEF DESCRIPTION OF THE DRAWINGS

FIG. 1 shows the relationship between the baseline blood pressure and the decrease in systolic pressure for individual with Metabolic Syndrome being treated with the grape extract used in the present invention.

FIG. 2 shows the relationship between the baseline blood pressure and the decrease in diastolic pressure for individual with Metabolic Syndrome being treated with the grape extract used in the present invention.

FIG. 3 shows the change in oxidized LDL concentration in individuals with Metabolic Syndrome being treated with the grape extract used in the present invention.

FIG. 4 shows the relationship between the change in oxidized LDL concentration and the baseline concentration of oxidized LDL in individuals given 300 mg of the grape extract used in the present invention.

DETAILED DESCRIPTION

The present invention provides a method of preventing and/or treating Metabolic Syndrome and/or the conditions that comprise Metabolic Syndrome. This method includes administering to a mammal, including a human, in need of such treatment a dietary supplement comprising an effective amount of grape extract. In particular, the grape extract used in the present method is effective to lower blood pressure and reduce oxidized LDL cholesterol in individual with Metabolic Syndrome.

The present invention also provides a method of treating and/or preventing Metabolic Syndrome in a mammal, comprising administering a dietary supplement comprising grape extract having about 5-15% monomers, about 5-20% dimers, about 3-10% trimers, about 2-10% tetramers, and about 2-10% pentamers by weight. The total amount of low molecular weight phenolic compounds including monomers, dimers, trimers, tetramers, and pentamers is between about 25-50% by weight, preferably between about 25-40% by weight, more preferably between about 30-40% by weight, and more preferably between about 25-35% by weight. The total amount of phenolic compounds is about 80% by weight or more, and preferably about 90% by weight or more.

The present invention also provides a method of preventing and/or treating pre-hypertension. This method includes administering to a mammal, including a human, in need of such treatment a dietary supplement comprising an effective amount of grape extract. In particular, the grape extract used in the present method is effective to lower blood pressure in pre-hypertensive individuals.

The present invention also provides a method of treating and/or preventing pre-hypertension in a mammal, comprising administering a dietary supplement comprising grape extract having about 5-15% monomers, about 5-20% dimers, about 3-10% trimers, about 2-10% tetramers, and about 2-10% pentamers by weight. The total amount of low molecular weight phenolic compounds including monomers, dimers, trimers, tetramers, and pentamers is between about 25-50% by weight, preferably between about 25-40% by weight, more preferably between about 30-40% by weight, and more preferably between about 25-35% by weight. The total amount of phenolic compounds is about 80% by weight or more, and preferably about 90% by weight or more.

The term "effective amount" means an amount of grape extract sufficient to decrease either or both systolic and/or diastolic blood pressure in pre-hypertensive individuals or those with Metabolic Syndrome by at least about 2%, preferably by at least about 5%, and more preferably by at least about 8%, without having adverse effects such. as increasing insulin resistance in the individual. An appropriate clinical end-point, however, is a systolic blood pressure below 120 mmHG in pre-hypertensive individuals or those with Metabolic Syndrome. It has also been suggested that the grape extract used in the present invention will, in addition to lowering blood pressure, reduce oxidized LDL cholesterol in individuals with Metabolic Syndrome. Increased LDL cholesterol is a recognized risk factor for atherosclerosis. There is strong evidence that oxidatively modified LDL initiates the development of this pathological process. Thus, decreasing the concentration of oxidized LDL may reduce and/or prevent atherosclerosis in individuals with Metabolic Syndrome.

The grape extract, to be used with the present invention, has a phenolic profile, as determined by normal-phase high-performance liquid chromatography ("HPLC"), of about 5-15% monomers, about 5-20% dimers, about 4-10% trimers, about 2-10% tetramers, and about 2-10% pentamers by weight. The grape extract used in the present invention also comprises about 80% by weight or more total phenolic compounds, and preferably about 90% by weight or more, as determined by the Folin Ciocalteu method. The grape extract used in the present invention also comprises about 2% by weight or less epicatechin-gallate terminal units, more preferably about 1% by weight or less, as determined by reverse-phase HPLC after thiolysis reaction. The grape extract used in the present invention also comprises about 12% by weight or less epicatechin-gallate extension units, preferably about 8% by weight or less, and more preferably about 5% by weight or less, as determined by reverse-phase HPLC after thiolysis reaction.

The grape extract used in the present invention may be produced by modifying the hot water extraction process disclosed in U.S. Pat. No. 6,544,581 as described below. In general, the hot water extraction process, as disclosed in the '581 patent, involves the following steps. In step (1), grape seeds, dry or fresh, may be heated with hot water for a time sufficient to extract most of the polyphenols. Temperatures of 140-212° F. may be employed, preferably 160-212° F., more preferably 180-212° F., yet more preferably 190-212° F., for a period of about 1-6 hours. The time of heating may be varied in relation to the temperature used. Generally, lower temperatures require longer extraction times. In step (2), the crude grape seed-water extract may be separated from spent seeds by draining over metal screens. The extract may then be cooled and treated with any suitable commercially available pectolytic enzyme, such as Pectinex® Ultra SP-L manufactured by Novo Nordisk, at a concentration of about 50-200 ppm to break down cell wall constituents. Preferably, the seed water extract may be enzyme-treated for a period of two hours at a temperature of 80-120° F. Alternatively, the seed-water extract may be enzyme-treated for 7-14 days or longer at about 40-50° F. In step (3), the resulting turbid seed extract may be acidified with an acid, preferably a mineral acid, more preferably with sulfuric acid, to a pH of approximately 1.5-2.5 and allowed to react from about one hour to about two days. The acidified extract may be cooled for up to several weeks to allow for macromolecules, including proteins and other polysaccharides, to settle. The cooled acidified extract may then be filtered using diatomaceous earth to yield a clarified seed extract. Other filter aids, such as perlite, may also be used.

Step (2) of the '581 patent may be modified by enzyme-treating the seed-water extract for a period of four to five days at a temperature of about 80-120° F. in order to produce the grape extract used in the present invention. While not intending to be bound to any theory, it is believed that the longer duration than used in the '581 patent at the specified temperature range of this step accounts for the resulting novel grape extract. The time of the enzyme treatment may be varied in relation to the temperature used. Generally, lower temperatures require longer treatment times. Thus, the seed-water extract may be enzyme-treated for up to two weeks or longer at temperatures of about 60-80° F.

Alternatively, the grape extract used in the present invention may be produced by the following steps. After the extraction of step (1) or after the pectinase treatment in step (2) of the '581 patent, the extract may be smeared on a bacteriological agar plate. Upon incubation, plural species of yeast, bacteria, and/or fungi may be present depending upon the starting material. The live culture may be isolated as a cocktail. Once isolated, the cocktail may be used in subsequent extraction and/or pectinase enzyme treatment steps. For instance, a seed-water extract may be enzyme treated with any suitable commercially available pectolytic enzyme and combined with the isolated cocktail of yeast, bacteria, and/or fungi. The combined mixture may be allowed to stand for a period of about one to ten days, preferably about two to five days, at a temperature of about 70-100° F. The time of the enzyme treatment may be varied in relation to the temperature used and the inoculum count. The resulting turbid seed extract may be acidified with a suitable acid as discussed above to a pH of 1.5-2.5 and allowed to react for about one hour to about two days. The acidified extract may be cooled and stored for several days to allow for flocculation of proteins and polysaccharides. The cool acidified extract may then be filtered using diatomaceous earth to yield a clarified seed extract, which may be further processed according to the '581 patent to produce a purified grape extract suitable for blood pressure reduction and reduction of oxidized LDL.

The amount of gallic acid in grape extracts produced by the '581 process as compared with grape extracts produced by the process involving a cocktail of yeast, bacteria, and/or fungi was analyzed by HPLC. Such analysis showed an increase from a value of between about 50-150 ppm of gallic acid in the grape extracts of the '581 process to a value of between about 400-1500 ppm of gallic acid in the grape extracts used in the present invention using the cocktail. The increase in gallic acid indicates that the epicatechin-gallate terminal and extension units are de-esterfied from procyanidins. While not intending to be bound to any theory, it is believed that the cocktail of yeast, bacteria, and/or fungi use the grape extract as a substrate for growth and produce tannase enzymatic activity, which results in de-esterification of procyanidins and release of gallic acid. As such, using a cocktail of live yeast, bacteria, and/or fungi produces the grape extract used in the present invention having about 2% by weight or less epicatechin-gallate terminal units, more preferably about 1% by weight or less, and about 12% by weight or less epicatechin-gallate extension units, preferably about 8% by weight or less, and more preferably about 5% by weight or less.

In one embodiment, the grape extract of the present invention may be produced by the following steps. After the extraction of step (1) or after the pectinase treatment in step (2) of the '581 patent, any suitable commercial fungal tannase enzyme, such as tannin acylhydrolase, E.C3.1.1.20, may be added at a concentration of between about 5-1000 ppm. Depending on the concentration of the tannase enzyme used, the mixture may be reacted for about one hour to about two days, preferably one to two days, or until the terminal units are reduced to about 2% or less, preferably 1% or less, and the extension units are reduced to about 8% or less, preferably about 5% or less. After a sufficient reaction time, the extract may be acidified to a pH of 1.5 to 2.5, which allows flocculation of proteins and polysaccharides on cooler storage from 40-60° F. The extract may be filtered to clarify and processed further according to the '581 patent to produce a grape extract with characteristics for blood pressure reduction.

The grape extract used in the present invention may be formulated into dietary supplements, including capsules, tablets, powders, solutions, gels, suspensions, creams, pastes, gels, suppositories, transdermal patches, and the like. These dietary supplements in, for instance, powder or solution form, may be added to nutraceuticals, foods and/or beverages to form functional nutraceutical, food, and/or beverage products. The dietary supplements may be formulated as powders, for example, for mixing with consumable liquids such as milk, juice, water or consumable gels or syrups for mixing into other dietary liquids or foods. The dietary supplements of this invention may be formulated with other foods or liquids to provide pre-measured supplemental foods, such as single serving bars. Typical food products that may incorporate the grape extract used in the present invention include dairy foods such as yogurt, cereals, breads, snack food products, fruit juices and other soft drinks. Flavorings, binders, protein, complex carbohydrates, vitamins, minerals and the like may be added as needed. Preferably, the grape extract is formulated for oral administration.

The dietary supplements used in the present invention are intended for daily administration or as needed. The magnitude of a prophylactic or therapeutic dose of the dietary supplement in pre-hypertensive individuals or those with Metabolic Syndrome will vary with the severity of the condition being treated and the route of administration. The dose, and perhaps the dose frequency, will also vary according to the age, body weight, and response of the individual. In general, the total daily dose range, for the conditions described herein, is from about 50 mg to about 1,000 mg by weight of grape extract administered in single or divided doses orally, topically, or transdermally, preferably orally. A preferred oral daily dose range is from about 50 mg to about 500 mg by weight of the grape extract (i.e., excluding excipients and carriers), more preferably about 150 mg to about 300 mg. For example, capsules or tablets may be formulated in either 150 mg or 300 mg doses, whereas beverages can be formulated with 50 mg grape extract. Such a regimen of administration is preferably maintained for at least one month, more preferably six months or longer.

The dietary supplements used in the present invention may be formulated in a conventional manner (e.g., wet or dry granulation), in admixture with pharmaceutically acceptable carriers, excipients, vitamins, minerals and/or other nutrients. Representative carriers and excipients include, but are not limited to, starches, sugars, microcrystalline cellulose, diluents, granulating agents, lubricants, binders, disintegrating agents, and the like, in the case of oral solid preparations (such as powders, capsules, and tablets).

Any suitable route of administration may be employed to administer the dietary supplements of the invention to an individual. Suitable routes include, for example, oral, rectal, parenteral, intravenous, topical, transdermal, subcutaneous, and intramuscular. Although any suitable route of administration may be employed for providing the individual with an effective amount of the grape extract according to the methods of the present invention, oral administration is preferred, including solid dosage forms such as tablets, capsules, or powders. It is also preferred that the grape extract is formulated for use in functional nutraceutical, food, or beverage products.

The grape extract used in the present invention can also be combined with other active agents including but not limited to diuretics, beta-blockers, ACE inhibitors, angiotensin antagonists, calcium channel blockers, alpha-blockers, alpha-beta-blockers, nervous system inhibitors, vasodilators, antioxidants.

1. Characterization of Grape Extracts

Recently, it was reported that the use of grape seed polyphenols does not reduce systolic blood pressure and actually increases systolic blood pressure when combined with the use of vitamin C in hypertensive individuals. See Ward et al. "The combination of vitamin C and grape-seed polyphenols increases blood pressure: a randomized, double-blind, placebo-controlled trial," *Journal of Hypertension* 2005; 23:427434. While not intending to be bound to any theory, it is believed that the phenolic profile of grape extracts is important to their effectiveness in reducing blood pressure. The grape extract evaluated in the Ward study was Vinlife®, which has a phenolic profile of 50.6% total phenolic compounds, as determined by Folin Ciocalteu method, 11.2% epicatechin-gallate terminal units, and 11.8% epicatechin-gallate extension units, as determined by reverse-phase HPLC after thiolysis reaction, and 7.3% monomers, 4.4% dimers, 2.0% trimers, 1.9% tetramers, and 1.1% pentamers, with a total monomers to pentamers of 16.7%, as determined by normal-phase HPLC.

Commercially available extracts of grape seed contain a variety of monomers and proanthocyanidins. The phenolic profile of some commercially available extracts, as determined by reverse-phase HPLC, is described in Table 1, and as determined by normal-phase HPLC, is described in Table 2. From these analyses, the grape extract used in the present invention (currently manufactured by Polyphenolics, Inc. as MegaNatural®-BP) has three differentiating factors that distinguish it from other grape extracts:

1. High degree of purity as determined by having an amount of the total phenolic compound greater than about 80% by weight, and more preferably greater than about 90% by weight, as determined by the Folin Ciocalteu method;
2. High amount, e.g. between about 25-50% by weight, of low molecular weight phenolic compounds, wherein low molecular weight phenolic compounds are monomers, dimers, trimers, tetramers, and pentamers; and,
3. Little to no amount, e.g. less than about 2%, preferably less than about 1%, of epicatechin-gallate in terminal units and a small amount, e.g. less than about 12%, preferably less than about 5%, of epicatechin-gallate in extension units.

Again, while not intending to be bound by any theory, it is believed that the phenolic profile of grape extracts is important to their effectiveness in treating or preventing pre-hypertension or Metabolic Syndrome in individuals. In particular, it is believed that the absence of epicatechin-gallate in terminal units and the small amount of epicatechin-gallate in extension units of the grape extract used in the present invention along with the presence of a higher amount of low molecular weight compounds is responsible for increased vasodilatation, which is believed to be responsible for the drop of blood pressure in the clinical studies of individuals with Metabolic Syndrome and pre-hypertension described below.

Reverse-Phase HPLC Procedure to Determine Percent of Monomers, Oligomers, and Polymers Reverse-phase HPLC analysis of grape extract can be used to determine the proportion of monomers, oligomers and polymers based on peak area at 280 nm.

HPLC conditions:

| Mobile Phase: | A: 2% glacial acetic acid |||| 
|---|---|---|---|---|
| | B: 80% acetonitrile, 0.4% acetic acid ||||
| Gradient: | Time ||||
| | (min) | % A | % B | Curve |
| | 0.00 | 100 | 0 | — |
| | 3.00 | 100 | 0 | 6 |
| | 6.00 | 96 | 4 | 6 |
| | 15.00 | 90 | 10 | 6 |
| | 30.00 | 85 | 15 | 6 |
| | 50.00 | 77 | 23 | 6 |
| | 60.00 | 75 | 25 | 6 |
| | 66.00 | 70 | 30 | 6 |
| | 80.00 | 50 | 50 | 6 |
| | 83.00 | 20 | 80 | 6 |
| | 85.00 | 100 | 0 | 6 |
| | 105.00 | 100 | 0 | 6 |
| | 110.00 | 100 | 0 | 6 |
| Column: | 250 mm × 4.6 mm, Prodigy 5μ ODS (3) 100 Å ||||
| | (Phenomenex, Torrance, CA) ||||
| Flow rate: | 1.0 mL/min ||||
| Detection wavelength: | 280 nm ||||
| Temperature: | 30° C. ||||
| Injection: | 25 μL ||||

Sample preparation: Accurately weigh 0.1 g grape extract into a 100 mL volumetric flask. Dissolve the sample in a small amount of methanol (≦5 mL), sonicate if necessary. Fill to volume with 18 Megaohm water. Centrifuge the sample (14,000 rpm, 10 min) or filter through 0.45 μM glass filter prior to injection. Determination for percent by weight monomers, oligomers and polymers is based on the peak area and concentration of the standards.

Method to Determine Terminal and Extensional Units of Proanthocyanidins Based on HPLC Analysis After Thiolysis Reaction Thiolysis is a method to determine average molecular size (degree of polymerization) and basic structure of proanthocyanidins in grape extracts. The information provided may indicate biological quality of grape extract for nutritional absorption in the body.

Thiolysis reagent: 5% phenyl methanethiol (benzyl mercaptan) in methanol containing 0.2 N HCl.

Condition: 0.1% Grape extract methanol solution was mixed with an equal volume of thiolysis reagent, stirred, and heated at 90° C. for 2 min. Water was added to stop the reaction. The reactant was then centrifuged at 14000 rpm for 2 min. The supernatant was analyzed directly by HPLC.

HPLC conditions:

| Mobile Phase: | A: 10% acetic acid/0.1% TFA/5% acetonitrile/84.9% water (v/v/v/v) |
|---|---|
| | B: acetonitrile |
| Gradient: | 0-30 min  0-50% B |
| | 30-35 min  50-100% B |
| Column: | 150 cm × 2.0 mm i.d., 4 μm Synergi hydro-RP 80 Å (Phenomenex, Torrance, CA) |
| Flow rate: | 0.3 mL/min |
| Detection wavelength: | HP 1100 FLD with excitation @ 276 nm and emission @ 316 nm and HP DAD at 280 nm |
| Temperature: | 30° C. |
| Injection: | 1-3 μL |

The grape extracts to be analyzed were dissolved in methanol, mixed with an equal volume of thiolytic reagent and heated for 2 min at 90° C. The released units were identified by mass spectrometry and quantitatively determined by HPLC under the conditions above. The average degree of polymerization was measured by calculating the molar ratio of all flavan-3-ol units (thioether adducts plus terminal units) to catechin, epicatechin and epicatechin-gallate corresponding to terminal units. The percentage of epicatechin gallate terminal units were determined based on molar ratio of epicatechin gallate in the sum of total moles of terminal units, which includes catechin, epicatechin and epicatechin gallate. The percentage of epicatechin-gallate extension units were determined based on molar ratio of epicatechin gallate thioether adducts in the sum of total moles of thioether adducts of extension units, which include catechin, epicatechin and epicatechin-gallate thioether adducts. The total amount of phenolic compounds was quantified in terms of grams Gallic Acid Equivalents (GAE) by the Folin Ciocalteu method. For more details on the Folin Ciocalteu analysis procedure, see: Waterhouse, A. L., *Determination of Total Phenolics, in Current Protocols in Food Analytical Chemistry*, I1.1.1-I1.1.8, Wrolstad, R. E., Wiley, 2001, or Singleton, V. L.; Orthofer, R.; Lamuela-Raventos, R. M. "Analysis of total phenols and other oxidation substrates and antioxidants by means of Folin-Ciocalteu Reagent," *Methods in Enzymology* 1999, 299, 152-178, both of which are incorporated herein by reference.

TABLE 1

Comparative Characteristics of MegaNatural ®-BP and Other Grape Extracts in the Market as Determined by Reverse-Phase HPLC

| Origin | Product Name | Total Phenol | Epicatechin-gallate Terminal | Epicatechin-gallate Extension | Determined by reverse-phase HPLC using peak area | | |
|---|---|---|---|---|---|---|---|
| | | g GAE/100 g (as is) | (%) | (%) | Monomers (%) | Oligomers (%) | Polymers (%) |
| USA | MegaNatural ®-BP | 93.8 | 0.0 | 6.8 | 12.8 | 62.6 | 24.6 |
| USA | MegaNatural ®-BP | 91.0 | 0.0 | 5.4 | 9.2 | 69.6 | 21.2 |
| USA | MegaNatural ®-BP | 95.2 | 0.0 | 6.9 | 13.8 | 64.7 | 21.5 |
| USA | MegaNatural ®-BP | 98.6 | 0.0 | 8.2 | 11.3 | 68.0 | 20.7 |
| USA | MegaNatural ®-BP | 91.1 | 0.0 | 5.4 | 5.4 | 71.5 | 23.2 |

TABLE 1-continued

Comparative Characteristics of MegaNatural ®-BP and Other Grape Extracts in the Market as Determined by Reverse-Phase HPLC

| | | Total Phenol | Epicatechin-gallate | Epicatechin-gallate | Determined by reverse-phase HPLC using peak area | | |
|---|---|---|---|---|---|---|---|
| Origin | Product Name | g GAE/100 g (as is) | Terminal (%) | Extension (%) | Monomers (%) | Oligomers (%) | Polymers (%) |
| USA | MegaNatural ®-BP | 95.5 | 0.0 | 5.1 | 6.5 | 73.3 | 20.3 |
| USA | MegaNatural ®-BP | 92.7 | 0.0 | 3.0 | 8.5 | 69.8 | 21.7 |
| USA | MegaNatural ®-BP | 93.5 | 0.0 | 4.8 | 5.4 | 69.9 | 24.7 |
| USA | MegaNatural Gold ® | 93.0 | 10.5 | 11.7 | 7.8 | 74.7 | 17.6 |
| USA | MegaNatural Gold ® | 91.9 | 4.3 | 14.6 | 12.3 | 76.7 | 11.0 |
| USA | MegaNatural Gold ® | 92.4 | 11.0 | 11.9 | 10.2 | 77.7 | 12.1 |
| USA | MegaNatural Gold ® | 89.1 | 5.2 | 12.9 | 9.9 | 73.7 | 16.4 |
| USA | MegaNatural Gold ® | 90.1 | 3.6 | 14.5 | 11.1 | 73.4 | 15.6 |
| USA | MegaNatural Gold ® | 90.3 | 2.8 | 8.8 | 13.2 | 65.5 | 21.3 |
| USA | MegaNatural Gold ® | 89.6 | 8.7 | 11.8 | 10.0 | 65.2 | 24.8 |
| Australia | Vinlife ® | 50.6 | 11.2 | 11.8 | 6.3 | 60.6 | 33.1 |
| Europe | Masquelier OPC ® | 98.0 | 8.5 | 7.5 | 12.1 | 68.4 | 19.5 |
| Europe | Naturex ® | 78.5 | 8.3 | 6.2 | 6.3 | 64.2 | 29.5 |
| Europe | Indena ® | 93.0 | 10.5 | 8.8 | 10.1 | 64.4 | 25.5 |
| China | Lycome ® | 88.5 | 10.6 | 7.5 | 5.3 | 63.1 | 31.7 |
| China | Recovery ® | 95.8 | 3.9 | 5.4 | 9.1 | 58.4 | 32.5 |
| China | Grape P E ® | 92.6 | 9.8 | 6.8 | 3.6 | 51.9 | 44.4 |
| China | MA ® | 70.1 | 8.7 | 10.5 | 4.6 | 55.3 | 40.1 |
| USA | ME ® | 68.9 | 12.1 | 6.3 | 1.9 | 52.6 | 45.4 |
| USA | San Joaquin ® | 74.9 | 17.7 | 6.7 | 2.2 | 56.1 | 41.8 |
| USA | Activin ® | 84.3 | 14.8 | 11.1 | 3.0 | 55.9 | 41.1 |
| Japan | KIKKOMAN ® | 44.5 | 5.2 | 13.1 | 8.1 | 52.9 | 38.9 |

Normal-Phase HPLC Analysis for Proanthocyanidins

HPLC analysis of proanthocyanidins: Chromatographic analyses were performed on an HP 1100 series HPLC equipped with an autosample/injector, binary pump, column heater, diode array detector, fluorescence detector, and HP ChemStation for data collection and manipulation. Normal phase separations of proanthocyanidin oligomers were performed on a Phenomenex Luna Silica (2) column.

| Mobile Phase: | A: dichloromethane, methanol, water, and acetic acid (83:13:2:2 (v/v)) |
| | B: methanol, water, and acetic acid (96:2:2 (v/v)) |
| Gradient: | 0-30 min   linear 0-17.6% B |
| | 30-45 min   linear 17.6-30.7% B |
| | 45-50 min   linear 30.7-87.8% B |
| | 50-60 min   linear 87.8% B |
| Column: | Phenomenex LUNA Silica (3.0 × 150 mm; 3.0 μm) |
| Flow rate: | 0.5 mL/min |
| Detection: | HP 1100 FLD with excitation @ 276 nm |

-continued

| | and emission @ 316 nm |
| Temperature: | 25° C. |
| Injection: | 3 μL |

In all cases, the column was re-equilibrated between injections with equivalent of 5 mL of the initial mobile phase. Catechin standards were prepared and analyzed to establish a response calibration curve from which to calculate the concentration of proanthocyanidins in the samples. Relative response factors of dimers, trimers, tetramers and pentamers to monomers with fluorescence detection were reported by R. L. Prior and L. Gu, "Occurrence and biological significance of proanthocyanidins in American diet," *Phytochemistry* 2005, 66(18) 2264-2280, using standards isolated and purified from cocoa bean. These response factors were used to calculate dimers, trimers, tetramers and pentamers relative to monomers.

TABLE 2

Comparative Characteristics of MegaNatural ®-BP and Other Grape Extracts in the Market as Determined by Normal-Phase HPLC

| | | Determined by Normal-phase HPLC Using Catechin and Epicatechin Equivalent (% by weight) | | | | | | |
|---|---|---|---|---|---|---|---|---|
| Origin | Product Name | Monomers | Dimers | Trimers | Tetramers | Pentamers | Monomers to pentamers | Others |
| USA | MegaNatural ®-BP | 6.3 | 8.7 | 4.0 | 4.4 | 2.8 | 26.2 | 73.8 |
| USA | MegaNatural ®-BP | 9.1 | 13.6 | 5.6 | 6.2 | 3.5 | 38.1 | 61.9 |
| USA | MegaNatural ®-BP | 9.2 | 14.8 | 5.2 | 5.4 | 2.7 | 37.3 | 62.7 |
| USA | MegaNatural ®-BP | 10.0 | 14.2 | 5.4 | 5.2 | 2.8 | 37.6 | 62.4 |
| USA | MegaNatural ®-BP | 7.5 | 11.9 | 5.2 | 5.5 | 3.4 | 33.4 | 66.6 |

TABLE 2-continued

Comparative Characteristics of MegaNatural ®-BP and Other Grape Extracts in the Market as Determined by Normal-Phase HPLC

| | | Determined by Normal-phase HPLC Using Catechin and Epicatechin Equivalent (% by weight) | | | | | | |
|---|---|---|---|---|---|---|---|---|
| Origin | Product Name | Monomers | Dimers | Trimers | Tetramers | Pentamers | Monomers to pentamers | Others |
| USA | MegaNatural ®-BP | 8.2 | 12.1 | 5.4 | 5.7 | 3.5 | 34.9 | 65.1 |
| USA | MegaNatural ®-BP | 9.0 | 11.3 | 5.4 | 4.7 | 2.5 | 32.9 | 67.1 |
| USA | MegaNatural ®-BP | 5.2 | 9.8 | 4.1 | 4.8 | 2.6 | 26.4 | 73.6 |
| Australia | Vinilife | 7.3 | 4.4 | 2.0 | 1.9 | 1.1 | 16.7 | 83.3 |
| Europe | Masquelier OPC ® | 15.5 | 14.2 | 6.2 | 4.8 | 2.9 | 43.6 | 56.4 |
| Europe | Naturex ® | 8.3 | 6.4 | 3.6 | 3.0 | 2.0 | 23.2 | 76.8 |
| Europe | Indena ® | 16.6 | 12.4 | 6.2 | 4.8 | 3.3 | 43.3 | 56.7 |
| China | Lycome ® | 7.6 | 6.2 | 3.4 | 2.8 | 1.9 | 22.0 | 78.0 |
| China | Recoverye ® | 17.5 | 8.1 | 4.4 | 2.8 | 2.0 | 34.8 | 65.2 |
| China | Grape P E ® | 3.9 | 3.2 | 1.9 | 1.5 | 1.1 | 11.6 | 88.4 |
| China | MA ® | 4.1 | 3.8 | 1.9 | 1.7 | 0.8 | 12.3 | 87.7 |
| USA | ME ® | 1.8 | 1.8 | 0.9 | 0.8 | 0.5 | 5.8 | 94.2 |
| USA | San Joaquin ® | 5.3 | 5.8 | 2.6 | 1.8 | 1.3 | 16.8 | 83.2 |
| USA | Activin ® | 5.5 | 4.8 | 2.1 | 1.3 | 1.3 | 15.1 | 84.9 |
| Japan | KiKKOMAN ® | 0.9 | 1.1 | 0.7 | 0.7 | 0.4 | 3.7 | 96.3 |

The results as set forth in Tables 1 and 2 were obtained using different methods, which account for the different ranges of, for example, the percent of monomers. For instance, reverse-phase HPLC was used to determine percentage of monomers, oligomers and polymers based on peak areas of these three groups of compounds. Gallaic acid is included as monomers. In the normal phase HPLC, catechin and epicatechin were used as standards to determine the amount of monomers, dimers, trimers, tetramers and pentamers in the grape extract by weight. The relative response factors of dimers, trimers, tetramers and pentamers related to monomers reported by R. L. Prior and L. Gu were used to calculate dimers, trimers, tetramers and pentamers.

2. Effect of Grape Extract on Blood Pressure of Individuals with Metabolic Syndrome The effects of grape extract used in the present invention on blood pressure were studied in twenty-four individuals diagnosed with Metabolic Syndrome. The study included an equal number of men and women between the ages of 20 and 50 years. Metabolic Syndrome was diagnosed on the basis of the criteria defined by the National Cholesterol Education Program Adult Treatment Panel III. Each subject exhibited at least three of the following features: 1) Fasting blood sugar >110 mg/dL, 2) HDL (<40 mg/dL in men and <45 mg/dL in women), 3) blood pressure >130/85, and 4) abdominal obesity (>102 cm for men and >88 cm for women). Individuals were excluded if they were current smokers or ex-smokers (<3 years); taking anti-inflammatory or hypertensive drugs; or consumed over-the-counter anti-oxidant compounds.

The individuals were block randomized into three groups of eight and they were given one of the following capsules depending on their group assignment.

Group 1 was given a placebo capsule

Group 2 was given a capsule containing 150 mg Grape Extract

Group 3 was given a capsule containing 300 mg Grape Extract

The individuals were given sufficient capsules to take the same dose once daily for the next twenty-eight days. At the end of this period, blood pressure measurements were obtained. Ambulatory blood pressures were recorded over a 12 hr period at the commencement of the study and again after four weeks. The procedure was non-invasive and involved placing a blood pressure cuff in the upper arm. The cuff was connected to an automated FDA-approved inflating device, which was worn on a belt.

Table 3 shows the blood pressure data for the three groups of individuals with Metabolic Syndrome. In those receiving 300 mg and 150 mg daily of the grape extract used in the present invention, there were significant reductions in both systolic and diastolic pressure. There were no significant changes in the group given placebo.

TABLE 3

Results of Grape Extract Used in the Present Invention on Blood Pressure of Individual with Metabolic Syndrome

| | 300 mg daily | | 150 mg daily | | Placebo | |
|---|---|---|---|---|---|---|
| | Systolic | Diastolic | Systolic | Diastolic | Systolic | Diastolic |
| Start | 129 ± 4 | 79 ± 3 | 137 ± 4 | 84 ± 3.3 | 124 ± 4 | 74 ± 4 |
| 4 weeks | 117 ± 3 | 71 ± 3 | 125 ± 4 | 78 ± 1.9 | 123 ± 4 | 71 ± 4 |
| p* | 0.007 | 0.006 | 0.003 | 0.009 | ns | ns |

*p is the probability that the start and end values are the same. A p of 0.05 or less (5%) is generally considered significant.

The relationship between the baseline blood pressure and the fall in both systolic and diastolic pressures are shown in FIGS. 1 and 2. Blood pressure is quoted as mmHg. Since the diagnosis of Metabolic Syndrome is based on the presence of three of the listed risk factors (one of which is blood pressure), the study did not block randomize the individuals for blood pressure. As such, the average pressures in the three groups were not similar (but varied within a narrow range).

This study demonstrates that the grape extract of the present invention in daily dosage of 150 mg and 300 mg lowers both systolic and diastolic blood pressure in individuals with Metabolic Syndrome. The fall in blood pressure is statistically significant for both doses of extract used. In fact, the changes in blood pressure observed with using grape extract were comparable to those observed in major clinical trials using pharmaceutical agents.

3. Effect of Grape Extract on Oxidized LDL of Individuals with Metabolic Syndrome The effects of grape extract used in the present invention on oxidized LDL were studied in the same twenty-four individuals diagnosed with Metabolic Syndrome as discussed above. The concentration of oxidized LDL was measured at the commencement of the study and again after four weeks of treatment. In order to measure the concentration of oxidized LDL, a blood sample was taken from each individual and analyzed.

The changes in concentration of oxidized LDL for the three groups are summarized in FIG. 3. FIG. 3 shows a slight drop in oxidized LDL for placebo, a trend drop in oxidized LDL for individuals taking 150 mg of the grape extract used in the present invention, and a statistically significant drop ($p<0.05$) in oxidized LDL for individuals taking 300 mg of the grape extract used in the present invention. FIG. 4 depicts the relationship between the change in oxidized LDL and the baseline concentration of oxidized LDL in individuals given 300 mg of the grape extract used in the study. The regression coefficient, $R^2$, =0.52. FIG. 4 shows a greater drop in oxidized LDL concentration in individuals who started with higher levels of oxidized LDL to begin with.

This study demonstrates that the grape extract of the present invention in daily dosage of 150 mg and 300 mg reduces oxidized LDL concentration in plasma in individuals with Metabolic Syndrome. Further, there was a statistically significant decrease in oxidized LDL concentration for those individuals given 300 mg of the grape extract used in the present invention.

4. Effect of Grape Extract on Individuals with Pre-Hypertension

The effects of grape extract used in the present invention were studied on twenty-four individuals diagnosed with pre-hypertension. The study included an equal number of men and women between the ages of 30 and 60 years. Pre-hypertension was diagnosed on the basis of the criteria defined by the Seventh Report of the Joint National Committee on Prevention, Detection, Evaluation, and Treatment of High Blood Pressure. Each subject had systolic pressure between 120 and 139 mmHg and/or diastolic pressure between 81 and 89 mmHG. Individuals were excluded if they were current smokers or ex-smokers (<3 years); taking anti-inflammatory or hypertensive drugs; or consumed over-the-counter antioxidant compounds.

The individuals were block randomized for gender into two groups of twelve and they were given one of the following capsules depending on their group assignment.

Group 1 was given a placebo capsule
Group 2 was given a capsule containing 300 mg MegaNatural®-BP The individuals were given sufficient capsules to take the same dose once daily for the next eight weeks. At the end of this period, blood pressure measurements were obtained. Ambulatory blood pressures were recorded over a 12 hr period at the commencement of the study and again after eight weeks. The procedure was non-invasive and involved placing a blood pressure cuff in the upper arm. The cuff was connected to an automated FDA-approved inflating device, which was worn on a belt.

Table 4 shows the blood pressure data for the two groups of individuals with pre-hypertension. The baseline pressures between the two groups were not significantly different. In those receiving 300 mg daily of the grape extract used in the present invention, there were significant reductions in both systolic and diastolic pressure; however, there were no significant changes in the group given placebo. For instance, the average drop in systolic blood pressure in the group treated with MegaNatural®-BP was 7.2±2.5 mmHg, whereas the systolic blood pressure in the placebo group increased by 0.03±1.5 mmHg. The data is summarized below. The values are given in mmHg (mean±SEM).

TABLE 4

Results of MegaNatural ®-BP on Blood Pressure of Individual with Pre-Hypertension

| | 300 mg MegaNatural ®-BP daily | | Placebo | |
|---|---|---|---|---|
| | Systolic | Diastolic | Systolic | Diastolic |
| Start | 133 ± 2 | 80 ± 2 | 134 ± 2 | 79 ± 2 |
| 8 weeks | 126 ± 2 | 73 ± 2 | 134 ± 2 | 80 ± 2 |
| p* | 0.021 | 0.042 | ns | ns |

*p is the probability that the start and end values are the same. A p of 0.05 or less (5%) is generally considered significant.

This study demonstrates that the grape extract of the present invention in daily dosage of 300 mg lowers both systolic and diastolic blood pressure in individuals with pre-hypertension. The fall in blood pressure is statistically significant. In fact, the changes in blood pressure observed with using grape extract were comparable to those observed in major clinical trials using pharmaceutical agents.

EXAMPLES

The invention is further defined by reference to the following examples describing a process for making the grape extract and preparing the dietary supplements. The examples are representative, and they should not be construed to limit the scope of the invention.

Example 1

Process for Making the Grape Extract

Dried grape seeds were extracted with water at a temperature of 200° F. for two hours and the extract was separated from the seeds on metal screens. The extract was cooled to 90-100° F. and pectinase was added at a concentration of 200 ppm. The extract was divided into two portions. To one portion, commercial fungal tannase enzyme (tannin acylhydrolase, E.C.3.1.1.20) was added at a concentration of 1000 ppm. To the second portion, the tannase was added at a concentration of 50 ppm. The residual concentration of gallic acid in the original extract was 117 ppm with 18.9% terminal units and 11.1% extension units. Within about two hours of treatment with 1000 ppm tannase enzyme, the gallic acid concentration rose to 904 ppm with 0% terminal units and about 5.5% extension units. It took about thirty-four hours of treatment with 50 ppm tannase enzyme for the gallic acid to reach 810 ppm with less than 1% terminal units and less than 6% extension units. After about two days, both the extracts were acidified to a pH of 1.5 to 2.5, which allowed flocculation of proteins and polysaccharides on cooler storage from 40-60° F. The extract was filtered and processed further according to the '581 patent to produce a grape extract with characteristics for blood pressure reduction and reduction of oxidized LDL concentrations.

Example 2

Capsules

MegaNatural®-BP grape extract (150 mg or 300 mg) was dry mixed with magnesium stearate (3 mg or 6 mg respectively) and loaded into hard shell gelatin capsules (made of gelatin and water). In the 150 mg formulation, the grape extract has a minimum of 90% phenols or 135 mg of phenols per 150 mg of grape extract. In the 300 mg formulation, the grape extract has a minimum of 90% phenols or 270 mg of phenols per 300 mg of grape extract. The daily dosage is one capsule per day.

Example 3

Powder

MegaNatural®-BP grape extract was formulated into a dry mix with the excipients as shown in Table 4 to be used in a beverage, wherein the ingredients were dry blended. To prepare the final beverage, 9.47 g of the dry mix is combined with 500 mL of cold water and stirred. A 500 mL serving contains 16 calories. The final beverage contains 100 mg MegaNatural®-BP grape extract and 120 mg vitamin C per 1 L serving, which will have an ORAC value of 2200 TE.

ORAC, measured in mmoles Trolox (a noncommercial, water-soluble derivative of tocopherol) equivalents (TE) per gram, stands for "Oxygen Radical Absorbance Capacity." This is the standard by which scientists measure antioxidant activity in foods and supplements. A single servings of fresh or freshly cooked fruits and vegetables supply an average of 600 to 800 ORAC units. It has been suggested that increasing intake of foods or supplements that provide 2,000 to 5,000 ORAC units per day may have health benefits.

TABLE 4

| Ingredients | % Dry Mix (g) |
| --- | --- |
| Maltodextrin | 37.48 |
| Citric Acid | 29.99 |
| Clouding Agent (Purity Gum 2000)* | 5.25 |
| Aspartame | 3.85 |
| Sodium Citrate, FCC Grade | 3.75 |
| Ultra Guar** | 3.75 |
| N&A Orange Flavor (SN313897)*** | 7.5 |
| Nat FF Passion Fruit Flavor (SN 313898)*** | 4.27 |
| FD&C Yellow #6(20:1 in Maltodextrin) | 2.24 |
| FD&C Yellow #5(20:1 in Maltodextrin) | 0.75 |
| Ascorbic Acid | 0.64 |
| MegaNatural ®-BP Grape Extract (Polyphenolics, Inc.) | 0.53 |
| TOTAL | 100 |

*Available from National Starch & Chemical Corporation, Bridgewater, NJ
**Available From P. L. Thomas & Co., Inc. Morristown, NJ
***Available from International Flavors & Fragrances, Dayton, NJ

Example 4

Beverage

MegaNatural®-BP grape extract was formulated into a beverage with the excipients as shown in Table 5. The following beverage contains 50 mg MegaNatural®-BP grape extract and 60 mg vitamin C (100% RDI) per 8 fl oz serving. In an 8 fl oz serving, the beverage contains 0 calories and 0.15 g total carbohydrates. A 16 fl oz serving would have an ORAC value of 2200 TE.

TABLE 5

| Ingredients | % by weight |
| --- | --- |
| Water | 99.4373 |
| Citric Acid | 0.2640 |
| MegaNatural Purple Color (Canandaigua Conc.) | 0.0528 |
| Sethness - Greenleaf Flavor System | 0.0867 |
| Sodium Benzoate | 0.0448 |
| Potassium Sorbate | 0.0448 |
| Ascorbic Acid | 0.0338 |
| MegaNatural ®-BP Grape Extract (Polyphenolics, Inc.) | 0.0211 |
| Asparatame | 0.0147 |
| TOTAL | 100.0000% |

Example 5

Beverage

MegaNatural®-BP grape extract was formulated into a beverage with the excipients as shown in Table 6. The following beverage contains 50 mg MegaNatural®-BP grape extract and 60 mg vitamin C (100% RDI) per 8 fl oz serving. In an 8 fl oz serving, the beverage contains 15 calories and 4 g total carbohydrates. A 16 fl oz serving would have an ORAC value of 2200 TE.

TABLE 6

| Ingredients | % by weight |
| --- | --- |
| Water | 95.8778 |
| Orange Juice Concentrate 65 | 1.3973 |
| Cranberry Juice Concentrate 50 | 0.8691 |
| MegaNatural Purple Color (Canandaigua Conc.) | 0.5032 |
| Sethness - Greenleaf Flavor System | 1.1074 |
| Sodium Benzoate | 0.0444 |
| Potassium Sorbate | 0.0444 |
| Ascorbic Acid | 0.0357 |
| MegaNatural ®-BP Grape Extract (Polyphenolics, Inc.) | 0.0210 |
| Neotame (The NutraSweet Co.) | 0.0997 |
| TOTAL | 100.0000% |

Example 6

Vitamin/Mineral Supplement

MegaNatura®-BP grape extract (150 mg) was dry mixed with the following excipients listed in Table 7 and pressed into a tablet to form a multi-vitamin/mineral supplement. The daily dosage is one tablet per day, preferably taken with food.

TABLE 7

| Ingredients | % Daily Value |
| --- | --- |
| Vitamin A 3500 IU (29% as Beta Carotene) | 70 |
| Vitamin C 60 mg | 100 |
| Vitamin D 400 IU | 100 |
| Vitamin E 45 IU | 150 |
| Vitamin K 10 mcg | 13 |
| Thiamin 1.5 mg | 100 |
| Riboflavin 1.7 mg | 100 |
| Niacin 20 mg | 100 |

TABLE 7-continued

| Ingredients | % Daily Value |
|---|---|
| Vitamin B6 3 mg | 150 |
| Folic Acid 400 mcg | 100 |
| Vitamin B12 25 mcg | 417 |
| Biotin 30 mcg | 10 |
| Pantothenic Acid 10 mg | 100 |
| Calcium 299 mg | 20 |
| Phosphorus 48 mg | 5 |
| Iodine 150 mcg | 100 |
| Magnesium 100 mg | 25 |

TABLE 7-continued

| Ingredients | % Daily Value |
|---|---|
| Zinc 15 mg | 100 |
| Selenium 20 mg | 29 |
| Copper 2 mg | 100 |
| Manganese 2 mg | 100 |
| Chromium 150 mcg | 125 |
| Molydenum 75 mcg | 100 |
| Chloride 72 mg | 2 |
| Potassium 80 mg | 2 |
| MegaNatural ®-BP Grape Extract 150 mg | * |
| Boron 150 mcg | * |
| Nickel 5 mcg | * |
| Silicon 2 mg | * |
| Vanadium 10 mcg | * |
| Lutein 250 mcg | * |
| Lycopene 300 mcg | * |

*Daily Value (% DV) not established

Example 7

Vitamin/Mineral Supplement

MegaNatural®-BP grape extract (150 mg) was blended with the following ingredients and excipients listed in Table 8 in V blender until uniform. The blend was pressed into tablets that reach a specified weight of 775 mg±2% to form a multivitamin/mineral supplement. The tablets were spray coated with a clear coating of a water soluble gum such as hydroxypropyl methylcellulose and dried. The daily dosage is one tablet per day. The batch size for the formulation in Table 8 is 500,000 Tablets.

TABLE 8

| Ingredients (Units of Measure) | Label Claim | Overage (%)* | Amount/ Tablet (mg) | Amount/ Batch (Kg) |
|---|---|---|---|---|
| Vitamin A Palmitate @ 500 K IU/gm (IU) | 5000 IU | 30 | 13.000 | 6.500 |
| Vitamin $D_3$ @ 850K IU/g (IU) | 400 IU | 30 | 0.612 | 0.306 |
| Vitamin E succinate (D-α) @ 1210 IU/g (IU) | 15 IU | 5 | 13.017 | 6.508 |
| Vitamin C (mg) | 30 mg | 2 | 30.600 | 15.300 |
| Thiamine HCl @ 89.2% (mg) | 1.5 mg | 2 | 1.715 | 0.858 |
| Riboflavin (mg) | 1.7 mg | 2 | 1.734 | 0.867 |
| Niacinamide (mg) | 10 mg | 2 | 10.200 | 5.100 |
| Pyridoxine HCl 82.3% (mg) | 2 mg | 5 | 2.552 | 1.276 |
| Folic Acid Trituration 1.0% (mcg) | 400 mcg | 25 | 50.000 | 25.000 |
| Vitamin B-12 Trituration 1.0% (mcg) | 6 mcg | 20 | 0.720 | 0.360 |
| Pantothenic Acid (Cal Pan.) (mg) | 10 mg | 5 | 10.500 | 5.250 |
| Biotin Trituration 1.0% (mcg) | 30 mcg | 20 | 3.600 | 1.800 |
| Calcium (Dicalcium Phosphate) 29.46% (mg) | 100 mg | 0 | 344.119 | 172.060 |
| Phosphorus (Dicalcium Phosphate) 22.77% (mg) | 75 mg | 0 | 0.000 | 0.000 |
| Magnesium (MgO) 60.32% (mg) | 20 mg | 0 | 33.156 | 16.578 |
| Zinc (ZnO) 80.34 (mg) | 5 mg | 0 | 6.224 | 3.112 |
| Iodine (KI) 76.45% (mcg) | 150 mcg | 0 | 0.196 | 0.098 |
| Copper (Gluconate) 14.00% (mg) | 2 mg | 0 | 14.286 | 7.143 |
| Manganese (Gluconate) 12.34% (mg) | 2 mg | 0 | 16.207 | 8.104 |
| MegaNatural ®-BP Grape Extract | 150 mg | | 150.000 | 25.000 |
| Microcrystalline cellulose | | | 33.750 | 16.875 |
| Croscarmellose Sodium | | | 20.250 | 10.125 |
| Stearic Acid | | | 13.500 | 6.750 |
| Magnesium Stearate | | | 5.063 | 2.531 |
| TOTAL | | | 775.000 | 337.500 |

*Percent amount of ingredient over label claim used to reach the label claim amount.

The invention claimed is:

1. A method of treating Metabolic Syndrome in a mammal in need thereof, comprising administering to the mammal a composition comprising a polyphenol extract from grapes in an amount effective to lower blood pressure, wherein the extract comprises about 2% by weight or less epicatechin-gallate terminal units, and monomers, dimers, trimers, tetramers and pentamers in a total amount between about 25-50% by weight of the extract.

2. The method of claim 1, wherein the extract comprises about 80% by weight or more total phenolic compounds.

3. The method of claim 2, wherein the extract comprises about 12% by weight or less epicatechin-gallate extension units.

4. The method of claim 1, wherein the amount of extract in the composition is between about 50-1000 mg.

5. The method of claim 1, wherein the composition is formulated for oral administration.

6. The method of claim 5, wherein the composition is administered in a form selected from the group consisting of tablets, powders, liquids, capsules and gels.

7. The method of claim 5, wherein the composition is a food or a beverage product.

8. The method of claim 5, wherein the composition is a nutraceutical.

9. The method of claim 1, wherein the mammal is a human.

10. The method of claim 1, wherein the extract contains 400-1500 ppm of gallic acid.

11. A method of treating pre-hypertension in a mammal in need thereof, comprising administering to the mammal a composition comprising a polyphenol extract from grapes in an amount effective to lower blood pressure, wherein the extract comprises about 2% by weight or less epicatechin-gallate terminal units, and wherein the total amount of monomers, dimers, trimers, tetramers and pentamers is between about 25- 50% by weight.

12. The method of claim 11, wherein the extract comprises about 80% by weight or more total phenolic compounds.

13. The method of claim 12, wherein the extract comprises about 12% by weight or less epicatechin-gallate extension units.

14. The method of claim 11, wherein the amount of extract in the composition is between about 50-1000 mg.

15. The method of claim 11, wherein the composition is formulated for oral administration.

16. The method of claim 15, wherein the composition is administered in a form selected from the group consisting of tablets, powders, liquids, capsules and gels.

17. The method of claim 15, wherein the composition is a food or a beverage product.

18. The method of claim 15, wherein the composition is a nutraceutical.

19. The method of claim 11, wherein the mammal is a human.

20. The method of claim 11, wherein the extract contains 400-1500 ppm of gallic acid.

21. A method of treating Metabolic Syndrome in a mammal in need thereof, comprising administering to the mammal a composition comprising a polyphenol extract from grapes in an amount effective to reduce oxidized LDL cholesterol, wherein the extract comprises about 2% by weight or less epicatechin-gallate terminal units, and wherein the total amount of monomers, dimers, trimers, tetramers and pentamers is between about 25-50% by weight.

22. The method of claim 21, wherein the extract comprises about 80% by weight or more total phenolic compounds.

23. The method of claim 22, wherein the extract comprises about 12% by weight or less epicatechin-gallate extension units.

24. The method of claim 21, wherein the amount of extract in the composition is between about 50-1000 mg.

25. The method of claim 21, wherein the composition is formulated for oral administration.

26. The method of claim 25, wherein the composition is administered in a form selected from the group consisting of tablets, powders, liquids, capsules and gels.

27. The method of claim 25, wherein the composition is a food or a beverage product.

28. The method of claim 25, wherein the composition is a nutraceutical.

29. The method of claim 21, wherein the mammal is a human.

30. The method of claim 21, wherein the extract contains 400-1500 ppm of gallic acid.

31. A method of treating Metabolic Syndrome in a mammal in need thereof, comprising administering to the mammal a composition comprising a polyphenol extract from grapes having about 5-15% monomers, about 5-20% dimers, about 3-10% trimers, about 2-10% tetramers, and about 2-10% pentamers by weight, wherein the extract comprises about 2% by weight or less epicatechin-gallate terminal units.

32. The method of claim 31, wherein the extract contains 400-1500 ppm of gallic acid.

33. A method of treating pre-hypertension in a mammal in need thereof, comprising administering to the mammal a composition comprising a polyphenol extract from grapes having about 5-15% monomers, about 5-20% dimers, about 3-10% trimers, about 2-10% tetramers, and about 2-10% pentamers by weight, wherein the extract comprises about 2% by weight or less epicatechin-gallate terminal units.

34. The method of claim 33, wherein the extract contains 400-1500 ppm of gallic acid.

35. A method of treating Metabolic Syndrome in a mammal in need thereof, comprising administering to the mammal a composition comprising a polyphenol extract from grapes in an amount effective to lower blood pressure, wherein the extract comprises about 2% by weight or less epicatechin-gallate terminal units, and between about 5-15% monomers, about 5-20% dimers, about 3-10% trimers, about 2-10% tetramers, and about 2-10% pentamers by weight.

* * * * *